United States Patent [19]

Stambach et al.

[11] Patent Number: 4,645,772
[45] Date of Patent: Feb. 24, 1987

[54] LEVOROTATORY ENANTIOMERS OF DERIVATIVES OF 5,6,13,13A-TETRAHYDRO-8H-DIBENZO [A,G]QUINOLIZINE, PREPARATIVE PROCESS, PHARMACEUTICAL COMPOSITIONS CONTAINING THEM AND APPLICATION

[75] Inventors: Jean-Francois Stambach; Louis Jung, both of Strasbourg; Christiane Heitz; Claire Schott, both of Schiltigheim; Jean-Claude Stoclet, Strasbourg; Fabienne Schutz, Molsheim, all of France

[73] Assignee: Urpha, Paris, France

[21] Appl. No.: 644,723

[22] PCT Filed: Dec. 14, 1983

[86] PCT No.: PCT/FR83/00251
  § 371 Date: Aug. 14, 1984
  § 102(e) Date: Aug. 14, 1984

[87] PCT Pub. No.: WO84/02342
  PCT Pub. Date: Jun. 21, 1984

[30] Foreign Application Priority Data

Dec. 14, 1982 [FR] France ................ 82 20975

[51] Int. Cl.⁴ ............... C07D 471/22; C07D 491/22; A61K 31/435
[52] U.S. Cl. .................... 514/280; 546/48; 546/71; 514/284
[58] Field of Search ............. 546/71, 48; 514/280, 514/284

[56] References Cited

U.S. PATENT DOCUMENTS 3,426,027 2/1969 Muller et al. .............. 546/71

FOREIGN PATENT DOCUMENTS 0028959 5/1981 European Pat. Off. ........ 546/71
2469413 11/1979 France .................... 546/71
1004077 9/1965 United Kingdom ............ 546/71
1095881 12/1967 United Kingdom ............ 546/71
1199338 7/1970 United Kingdom ............ 546/71

OTHER PUBLICATIONS

Späth, E. et al, Chem. Ber., (1930) pp. 3007-3012.
Chem Abs., vol 82, 43626 u (p. 460) 1975.
Berichte der Deutschen Chemischen Gesellschaft, vol. 63, No. 358, pp. 2343-2347 (1930).

Primary Examiner—George F. Lesmes
Assistant Examiner—S. A. Gibson
Attorney, Agent, or Firm—Burns, Doane, Swecker & Mathis

[57] ABSTRACT

Levorotatory enantiomers of the derivatives of 5,6,13,13a-tetrahydro-8H-dibenzo-[a,g]-quinolizine of formula III

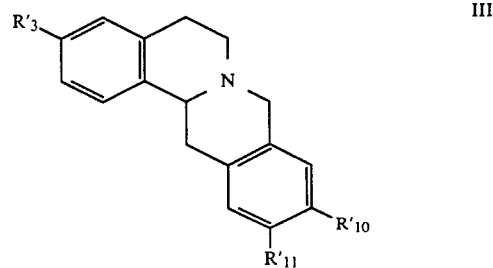

wherein
  $R'_3$ is hydrogen, an aryl or alkyl group or a —OR or —SR moiety wherein R is hydrogen, an aryl or alkyl group or a group of formula:

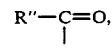

wherein R″ is an aryl or alkyl group,
  $R'_{10}$ and $R'_{11}$ which are identical or different, represent hydrogen, an aryloxy, alkoxy or hydroxy group or $R'_{10}$ and $R'_{11}$ taken together form a —O—(CH$_2$)$_n$—O— group in which n is 1 to 3.

Application to treatment of cardiovascular disorders.

6 Claims, 4 Drawing Figures

LEVOROTATORY ENANTIOMERS OF DERIVATIVES OF 5,6,13,13A-TETRAHYDRO-8H-DIBENZO [a,g]QUINOLIZINE, PREPARATIVE PROCESS, PHARMACEUTICAL COMPOSITIONS CONTAINING THEM AND APPLICATION

The present invention relates to the levorotatory enantiomers of derivatives of tetrahydro-5,6,13,13a-8H-dibenzo[a,g]quinolizine. It also relates to the preparation of the said enantiomers. The invention also provides the therapeutic use of these novel compounds and the pharmaceutical compositions containing them.

5,6,13,13a-tetrahydro-8H-dibenzo[a,g]quinolizine, whose non-proprietary name is "Berbine", has the formula I below:

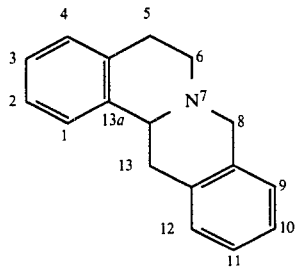

I

"Berbine" reverses the hypertensive effects of adrenalin in the dog (Raymond Hamet, Bulletin de l'Académie Nationale de Médecine 1952, 22 and 23, 408; Raymond Hamet, C. R. Acad. Sci. 1953, 236, 1916). L-Berbine has in the cat, as in the dog, a strong sympatholytic activity (Raymond Hamet, C. R. Acad. Sci. Paris, t 259 1964, p. 4397-4399). Berbine has hypotensive activity in hypertensive patients (Faquet, Lisles and Combaz, Gazette Médicale de France, 1954, 61, 1615). The separation of the enantiomers of Berbine as described by Wolfgang Leithe, Berichte 63 2343 (1930) is by successive crystallizations of certain of its salts with optically active acids, according to a conventional method.

The patent No. EP-A-0028959 describes the synthesis of a racemic mixture of certain derivatives of tetrahydro-5,6,13,13a-8H-dibenzo[a,g]quinolizine, as well as its use in the treatment of cardiovascular disorders, but the separation of the enantiomers, and/or their possible remarkable therapeutic properties are not suggested.

In the publication: Heterocycles (1974) 2(5) 625-30 the preparation of certain derivatives of Berbine is described from each of the distinct enantiomers, of the corresponding isoquinolines. The preparation process for each enantiomer is completely different from that according to the invention since the latter involves a stereospecific synthesis starting from each appropriately substituted isomer of isoquinoline. The tests described prove that the compounds thus obtained, which have the formula Ib below, do not have dopaminergic activity.

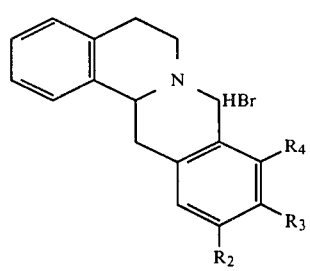

Ib in which if $R_4$ is H, $R_2$ and $R_3$ represent OH or $OCH_3$ and if $R_2$ is H, $R_3$ and $R_4$ represent OH.

Finally, the patent GB No. 1,004,077 provides compositions comprising dibenzoquinolizines which have tranquilizing, antidepressant and antiemetic activity. It is indicated that these dibenzoquinolizines can be in the racemic form or in d- or l-forms but the isolation of these latter forms is not described and their respective properties remain unknown.

These dibenzoquinolizines have the general formula below:

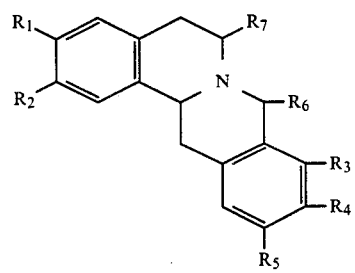

Ia in which
$R_1$ and $R_2$ represent hydrogen, hydroxy, methoxy or ethoxy;
$R_3$ and $R_5$ represent hydrogen or methoxy;
$R_4$ represents hydrogen, hydroxy, methoxy or ethoxy and
$R_6$ and $R_7$ represent hydrogen or methyl.

It should be noted that by the synthetic process described in this patent GB No. 1,004,077, it is not possible to obtain derivatives hydroxylated in position 3, that is to say the compounds of formula Ia above in which $R_1$ is hydroxy.

Indeed the operative conditions of the process mentioned on page 2, lines 59 to 64 of this patent GB No. 1,004,077 are too strong (acidity and heat) to avoid the decomposition of the benzyloxy group (protector of the hydroxy functional group) during the course of the cyclization reaction of the N-substituted phenylacetamides to 3,4 dihydroisoquinolines, carried out in the presence of phosphorus oxychloride and with heating.

In the patent application No. FR-A-2,469,413 in the name of the applicant, there was described derivatives of Berbine which have an interesting pharmacological activity, in particular in the cardiovascular area for the treatment of rhythm disorders and cardiac and coronary insufficiencies.

The derivatives of Berbine described in said patent application No. FR-A-2,469,413 have the general formula II:

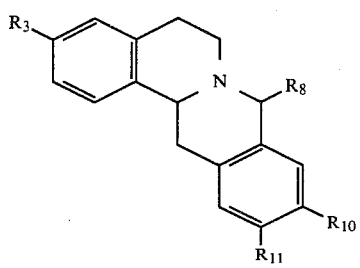

II

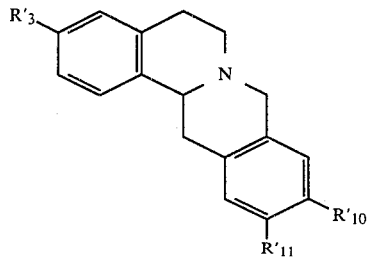

III in which:

R$_3$ is —OR or —SR in which R is hydrogen, an aryl or alkyl group or a group of formula

in which R' is an aryl or alkyl group:

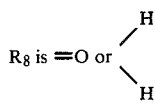

R$_{10}$ and R$_{11}$ are identical or different, and hydrogen or an aryloxy or lower alkoxy group provided that, when

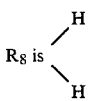

R$_{10}$ and R$_{11}$ are hydrogen or a lower alkoxy group, R$_3$ is different from the OR group in which R is an alkyl group.

It has now been found that the levorotatory enantiomers of derivatives of Berbine have a high hypotensive activity, they competitively inhibit the vasoconstrictor activity of phenylephrine, that is to say they have an α-blocking activity whereas the corresponding racemic forms behave as non-competitive antagonists of phenylephrine and can in consequence have undesirable side effects. Both of these activities are stereospecific. Unlike the dibenzoquinolizines which possess a tranquilizing, antidepressant and antiemetic activity (see the U.S. Pat. No. 1,004,077), the compounds according to the invention are suitable for therapeutic use in the treatment of cardiovascular disorders, in particular arterial hypertension and cardiac and coronary insufficiency.

The present invention relates then to the levorotatory enantiomers of derivatives of 5,6,13,13a-tetrahydro-8H-dibenzo[a,g]quinolizine (Berbine) and their pharmaceutically acceptable salts. The compounds of the invention have the general formula III:

in which:

R'$_3$ is hydrogen or an aryl or alkyl group or an —OR or —SR moiety in which R is hydrogen, an aryl or alkyl group or a group of formula:

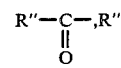

being a phenylalkyl, aryl or alkyl group.

R'$_{10}$ and R'$_{11}$, which are identical or different, represent hydrogen, an aryloxy, alkoxy or hydroxy group or R'$_{10}$ and R'$_{11}$ when taken together are —O—(CH$_2$)$_n$—O— in which n is 1 to 3, provided that R'$_3$, R'$_{10}$ and R'$_{11}$ are not simultaneously hydrogen and that if R'$_{10}$ and R'$_{11}$ are hydrogen or a lower alkoxy group, R'$_3$ is not an alkoxy group.

In the present specification, the term "alkyl" designates straight or branched C$_1$-C$_{12}$ aliphatic hydrocarbon groups. The lower alkyl groups are preferred, that is to say C$_1$-C$_4$ alkyl groups.

The term "aryl" designates the non-heterocyclic aromatic groups such as phenyl, benzyl and higher analogues, substituted or not, as well as heterocyclic aromatic groups with C$_4$-C$_7$ aromatic ring, and 1 to 4 heteroatoms that can be oxygen, nitrogen, sulfur, such as furan, pyridine, oxazole, as well as their saturated derivatives such as cyclohexane, tetrahydrofuran, piperidine and oxazolidine respectively.

The expression "lower alkoxy" designates the groups of formula R'$_a$—O in which R'$_a$ is a lower alkyl group, as defined above.

DETAILED DESCRIPTION OF THE INVENTION

Figure 1A:
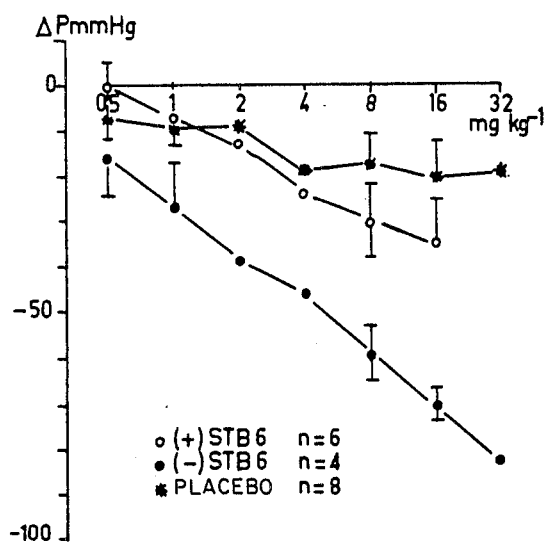
FIG. 1a and FIG. 1b show the effects on blood pressure of increasing doses of derivatives (+) and (−) STB 6 and (+) and (−) STB 4, respectively.

The compounds according to the invention are obtained from the corresponding racemic form by conventional separation procedures, by successive recrystallizations of a salt formed between the derivatives of Berbine in base form and an acid resolving agent from an appropriate solvent.

The racemic form of the derivatives of Berbine according to the invention are obtained, for example, by the process described in No. FR-A-2,469,413.

In general terms, this process of synthesis consists of:

(1) condensing, with nitromethane, benzaldehyde 3-substituted by a protected R'₃ group, to obtain the corresponding nitrostyrene;

(2) reducing the nitrostyrene obtained to obtain the corresponding phenethylamine;

(3) condensing the phenethylamine obtained with the substituted phenylacetic acid of formula:

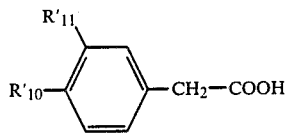

to obtain the corresponding phenacetamide;

(4) conducting a first cyclization to obtain the corresponding 3,4-dihydroisoquinoline;

(5) reducing the dihydroisoquinoline to the tetrahydroisoquinoline;

(6) fixing, by condensation with formic acid or phosgene, a formyl or chloroformyl group on the nitrogen atom of isoquinoline;

(7) conducting a second cyclization;

(8) reducing the reaction product to obtain the desired derivative of Berbine;

(9) eventually, eliminating the protecting group in position 3; and

(10) eventually, esterifying or etherifying the obtained compound.

As indicated above, the process of synthesis of compounds according to the invention comprises two possibilities at the level of step 6. One of the possibilities consists of the formylation of the tetrahydroisoquinoline obtained in step 5 and the other consists of the chloroformylation of the said tetrahydroisoquinoline which allows the preparation of the compounds of formula II in which R₈ is oxygen, the groups R'₃, R'₁₀ and R'₁₁ being those defined previously.

For further details about this process of synthesis of the different embodiments, reference can be made to No. FR-A-2,469,413, incorporated herein by reference.

The process according to the present invention for the recovery of pure optical isomers consists in reacting the amino group of the racemic, which is a base, with an appropriate acid resolving agent to form the salts of the two enantiomers and to recover the salt of the desired enantiomer by successive recrystallizations from an appropriate solvent.

Preferably, the acid used is:

(−) diparatoluoyl-L-tartaric acid, (+) diparatoluoyl-D-tartaric acid, which according to the case will permit the recovery of one or the other of the enantiomers.

The recrystallization solvents used according to the invention are, for example, methanol, ethanol, ethyl acetate, chloroform and similar compounds which are suitable for the recrystallization of the compound considered.

The pure optical isomers of formula III above in which R'₃ is hydroxy can be obtained by hydrolysis of the pure optical isomers of the corresponding compounds of formula III in which R'₃ is the group of formula R''—COO—. The hydrolysis is preferably carried out in acidic medium, for example in acetohydrochloric medium.

These pure optical isomers of the compounds of formula III in which R'₃ hydroxy can then be esterified to give other pure stereoisomers of the compounds according to the invention. Such an esterification can be carried out by reaction of the said compound of formula III with an acid chloride of formula

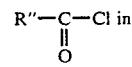

the presence of a base, such as triethylamine, in an appropriate solvent, such as chloroform. After recovery of the ester formed, it is recrystallized from an appropriate solvent; the product thus obtained has formula III in which R'₃ is a

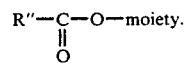

All the above steps are carried out at ambient temperature or at any other temperature suitable for these types of reactions that the man skilled in the art is able to determine by usual tests.

The compounds according to the invention possess interesting pharmacological properties, in particular in the cardiovascular area for the treatment of rhythm disorders, cardiac and coronary insufficiencies and arterial hypertension. The compounds of the invention, as previously mentioned, competitively inhibit the vasoconstrictor activity of phenylephrine, which is the following compound: (R)-3-hydroxy-α-[(methylamino)-methyl]benzenemethanol, and have an α-blocking activity, which is specific to the α₁ receptors for certain compounds of the invention, and a hypotensive activity.

The present invention therefore provides also the pharmaceutical compositions containing, as active ingredient, the levorotatory isomer of a compound of formula III in combination with a suitable carrier. The pharmaceutical compositions according to the invention can in particular be presented in dosage forms, suitable for oral or parenteral administration.

For oral administration, the compositions according to the invention can be used in the form of tablets, capsules, syrups, drops, the carriers used being known carriers for the production of these pharmaceutical forms, obviously inert with respect to the active ingredient. The therapeutic dose will depend on the disorder to be treated but in general 50 to 500 mg per day of the levorotatory isomers according to the invention are administered.

The invention will now be described in greater detail in the following non limiting examples. In these examples the racemic form prepared according to the process described in No. FR-A-2,469,413 were used as the starting compounds for the production of the isomers according to the invention. Thus, the compounds cited below, obtained by methods described in the examples of No. FR-A-2,469,413, were used as starting products.

| RACEMIC COMPOUND | REFERENCE | R'$_3$ | R'$_{10}$ | R'$_{11}$ | Example from the application prepared according to FR-A-2,469,413 |
|---|---|---|---|---|---|
| 3-hydroxy-5,6,13,13a-tetrahydro-8H—dibenzo[a, g]quinolizine or 3-hydroxy-berbine | STB 4 | HO | H | H | Example 5 |
| 10,11-dimethoxy-3-hydroxy-5,6,13,13a-tetrahydro-8H—dibenzo[a,g]quinolizine or 10,11-dimethoxy-3 hydroxy-berbine | STB 6 | HO | CH$_3$O | CH$_3$O | Example 1 |
| 10,11-dimethoxy-3-phenacetyloxy-5,6,13,13a-tetrahydro-8H—dibenzo[a, g]quinolizine or 10,11-dimethoxy-3-phenacetyloxy-berbine | STB 52 | C$_6$H$_5$CH$_2$CO$_2$ | CH$_3$O | CH$_3$O | Example 6 |
| 3-phenacetyloxy-5,6,13,13a-tetrahydro-8H—dibenzo [a, g]quinolizine or 3-phenacetyloxy-berbine | STB 9 | C$_6$H$_5$CH$_2$CO$_2$ | H | H | Example 6 |

For reasons of comparison the corresponding dextrorotatory isomers were also prepared.

EXAMPLE 1

Preparation of the pure optical isomers of 10,11-dimethoxy-3-hydroxy-5,6,13,13a-tetrahydro-8H-dibenzo-[a,g]-quinolizine or 10,11-dimethoxy-3-hydroxy-berbine (STB 6)

(−) Isomer STB 6

The recovery of the (−) enantiomer of STB 6 was carried out by successive recrystallizations from methanol of the salt formed from the STB 6 racemic and (−) diparatoluyl-L-tartaric acid.

After purification of the (−) salt, the (−) STB 6 free base is obtained by reaction on its salt of diluted ammoniumhydroxide and extraction in chloroform.

(+) Isomers STB 6

The (+) enantiomer of STB 6 was recovered in the same way as its optical antipode but by using (+) diparatoluyl D-tartaric acid as resolving agent. The solutions from the preceding recrystallizations are made basic and the racemic which is enriched in (+) isomer, is extracted.

EXAMPLE 2

Preparation of the pure optical isomers of 3-phenacetyloxy-5,6,13,13a-tetrahydro-8H-dibenzo-[a,g]-quinolizine or 3-phenacetyloxy-berbine STB 69 (−) and (+) Isomers STB 69

The (−) and (+) isomers of compound 69 were recovered in the same way as the (−) and (+) isomers of compound STB 6 by recrystallizations from ethyl acetate.

EXAMPLE 3

Preparation of the pure optical isomers of 3-hydroxy-5,6,13,13a-tetrahydro-8H-dibenzo-[a,g]-quinolizine or 3-hydroxy-berbine (−) and (+) Isomers STB 4

The (−) and (+) isomers of compound STB 4 are obtained by hydrolysis in acetohydrochloric medium of the pure optical isomers of compound STB 69 prepared previously.

EXAMPLE 4

Preparation of the pure optical isomers of 10,11-dimethoxy-3-phenacetyloxy-5,6,13,13a-tetrahydro-8H-dibenzo-[a,g]-quinolizine or 10,11-dimethoxy-3-phenacetyloxy-berbine (STB 52)

The (−) and (+) isomers of 10,11-dimethoxy-3-phenacetyloxy-5,6,13,13a-tetrahydro-dibenzo-[a,g]-quinolizine or 10,11-dimethoxy-3-phenacetyloxy-berbine STB 52 were obtained by esterification of compounds STB 6 (−) and (+) respectively.

According to the procedures described above the quantities of optically pure products obtained were the following:

| | |
|---|---|
| 11.5 g of STB 6 (−) isomer | from 50 g of racemic form |
| 10.2 g of STB 6 (+) isomer | |
| 6.0 g of STB 52 (−) isomer | |
| 4.0 g of STB 52 (+) isomer | |
| 7.2 g of STB 69 (−) isomer | from 35 g of racemic form |
| 4.6 g of STB 69 (+) isomer | |
| 3.4 g of STB 4 (−) isomer | |
| 1.9 g of STB 4 (+) isomer | |

In the following table are mentioned the specific rotation angles $[\alpha]_D^{20}$ (rotatory power) of the different optically active compounds recovered and their principal physico-chemical characteristics:

| Derivatives | Rotatory power $[\alpha]_D^{20}$ | | Concentration g/100 ml | Solvent | F° C. |
|---|---|---|---|---|---|
| | (+) | (−) | | | |
| STB 6, Base | +298° | −297° ↓ | | +CHCl$_3$ | 224° |
| | | | | −CHCl$_3$ | 226° |
| STB 6, HCl | +202° | −202° ↓ | | +Absolute EtOH | dep >200° |
| | | | | −Absolute EtOH | dep >200° |
| STB 52, Base | +230° | −232° ↓ | 0.2 | +CHCl$_3$ | 135° |
| | | | | −CHCl$_3$ | 136° |
| STB 52, HCl | +160° | −159° ↓ | | +Absolute EtOH | 206° |
| | | | | −Absolute EtOH | 205° |

-continued

| Derivatives | Rotatory power $[\alpha]_D^{20}$ (+) | (−) | Concentration g/100 ml | Solvent | F° C. |
|---|---|---|---|---|---|
| STB 69, Base | +250° | −249° ↓ | | +CHCl$_3$ | 115° |
| | | | | −CHCl$_3$ | 114° |
| STB 69, HCl | +198° | −199° ↓ | | +Absolute EtOH | 200° |
| | | | | −Absolute EtOH | 198° |
| STB 4, Base | +290° | −292° ↓ | | +CHCl$_3$ | 120-22° |
| | | | | −CHCl$_3$ | 120-22° |
| STB 4, HCl | +236° | −239° ↓ | | +95° EtOH | dep <200° |
| | | | | −95° EtOH | dep <200° | dep = decomposition

Pharmacological tests (1) Hypotensive activity:

The study was carried out in the normotensive rat anesthetized with pentothal (40 mg.kg$^{-1}$ i.p.). The blood pressure was measured with a catheter placed in the carotid artery and linked to a pressure cell (Statham p 23 DB) and to a recorder according to the method described by Waeldele and Stoclet (J. Pharmacol. Paris 1973, 66, 357–366). The derivatives were administered in increasing doses every 15 minutes by intravenous injection (i.v.).

FIG. 1 shows the effects on the blood pressure of increasing doses of the derivaties (+) and (−) STB 6 and (+) and (−) STB 4, 15 minutes after i.v. administration to an anesthetized normotensive rat. Each point is the average of the values obtained in n aminals ±standard error.

In FIG. 1 the abscissae show the quantities administered of the compound to be tested, and the ordinates show the average blood pressure ΔP mm Hg.

Figure 1B:
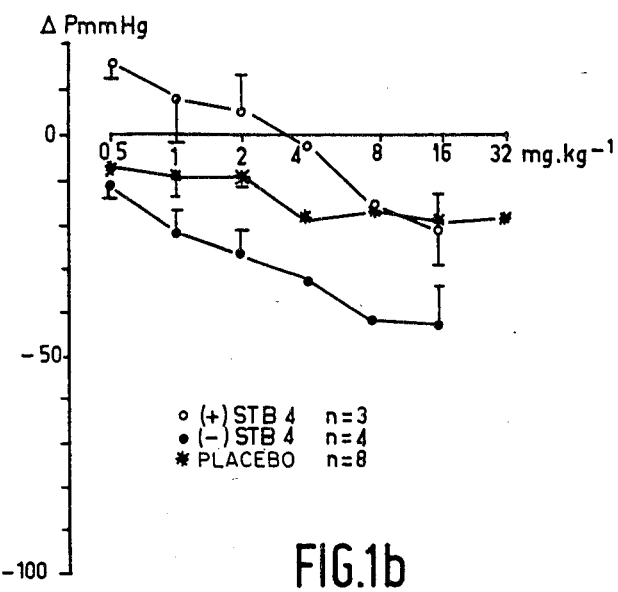

FIG. 1a relates to compound STB 6.
FIG. 1b relates to compound STB 4.

In both FIGS. 1a and 1b the ○—○ curves relate to the (+) isomers, the ●—● curves represent the (−) isomers and the x—x curves concern the placebos.

The results shown in FIG. 1 demonstrate that the (−) isomers of STB 6 and STB 4 produce a significant drop in blood pressure. The (−) STB 4 and above all the (−) STB 6 are active at low doses (1 mg. kg$^{-1}$ respectively).

In the same experimental conditions the (+) STB 6 and (+) STB 4 derivatives do not induce a significant decrease in blood pressure compared to the controls.

Figure 2A:
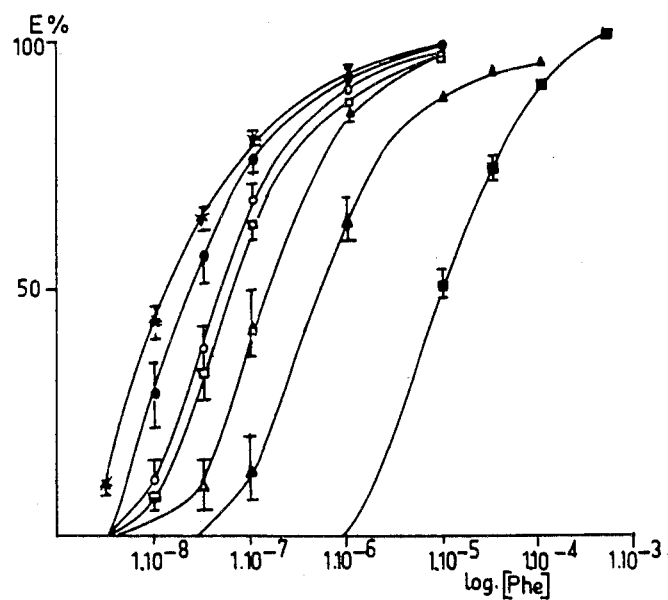
FIG. 2a and FIG. 2b illustrate the activity concentration relationships of (−) STB6 against phenylephrine.

(2) Study of α-blocking activity: study of the antagonism between the derivatives of Berbine and phenylephrine on the isolated rat aorta The quantitative evaluation of the antagonism between the derivatives to be tested and phenylephrine was made by analysis to effect-concentration relationships in the presence and absence of antagonist and the PA$_2$ values calculated with Schild's relation (Arunlaksksha na O. and Schild H. P., Br. J. Pharmacol., 1959, 14, 48–58). The study of activity concentration relationships against phenylephrine shows that the antagonism between (−) STB 6 and phenylephrine is competitive, as the results in FIG. 2 show. In FIG. 2 the E effect (% of maximum contraction) in the absence and presence of STB 6 (−) is given in the ordinate, and the abscissa gives the log of the phenylephrine concentration. The different curves relate to the following concentrations:

| curve ●—● | (−) STB 6, 5 · 10$^{-8}$ M |
|---|---|
| curve ○—○ | (−) STB 6, 10$^{-7}$ M |
| curve □—□ | (−) STB 6, 2.5 · 10$^{-7}$ M |
| curve △—△ | (−) STB 6, 5 · 10$^{-7}$ M |
| curve ▲—▲ | (−) STB 6, 10$^{-6}$ M |
| curve ■—■ | (−) STB 6, 10$^{-5}$ M |
| curve x—x | without STB 6. |

The values are the average of 6 experiments (±sm).

Figure 2B:
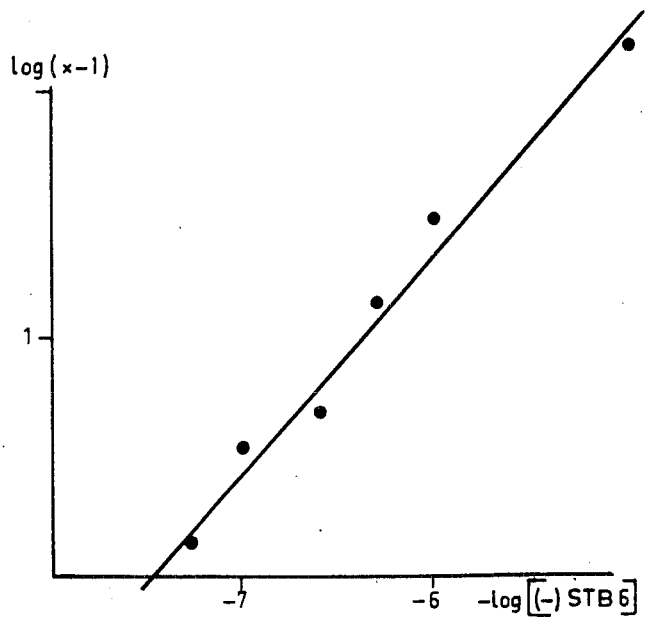

FIG. 2b is the Schild representation (x being the ratio of phenylephrine concentrations which gives a 50% response in the presence and in the absence of STB 6 (−)). On the ordinate are Log (x−1) and on the abscissa Log [(−) STB 6].

The parameters of Schild's relation were also measured in the presence of STB 52 (−) in the same experimental conditions as for STB 6 (−).

These parameters are given below.

Parameters of Schild's relation observed in the presence of (−) STB 52 and (−) STB 6:

| | pA$_2$ | n | r |
|---|---|---|---|
| (−) STB 52 | 7.0 | 1.00 | 0.99 |
| (−) STB 6 | 7.4 | 0.93 | 0.99 | n = slope of Schild's straight line
r = correlation coefficient of the straight line.

The above results show that (−) STB 52 is as competitive an antagonist of phenylephrine as (−) STB 6.

Figure 3:
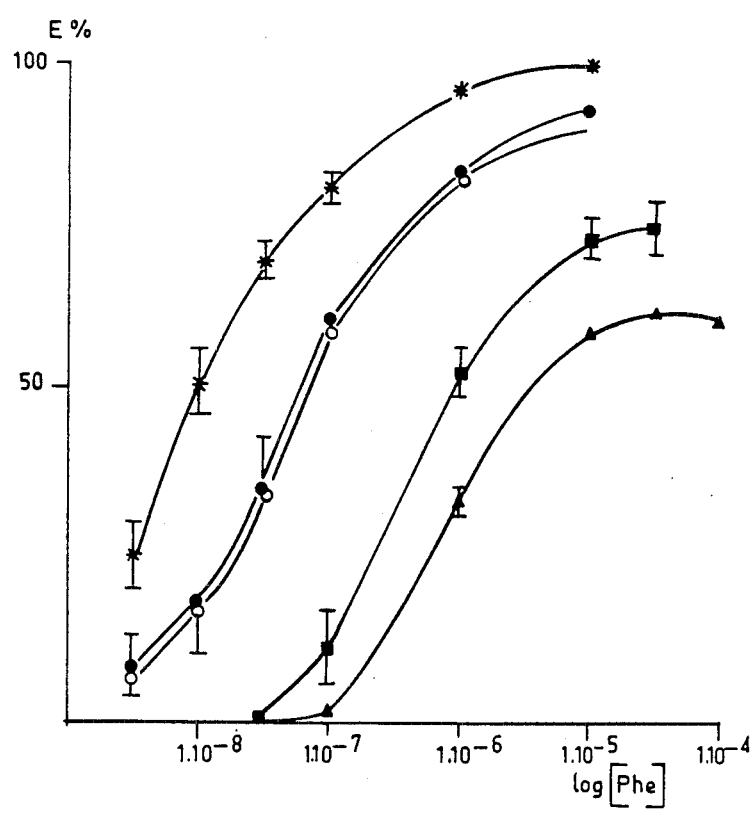
FIG. 3 illustrates the antagonism between (+) STB 6 and phenylephrine on isolated rat aorta.

The (−) derivatives of STB 6 and STB 52 have a strong affinity for the adrenergic receptor. In contrast the (+) STB 6 exhibited non-competitive antagonism against phenylephrine (FIG. 3). FIG. 3 represents the antagonism between (+) STB 6 and phenylephrine on the isolated rat aorta; in this figure the ordinate relates to the E effect (% of maximum contraction) in the absence and presence of (+) STB 6, and the abscissa represents the Log of the phenylephrine concentration.

The different curves represent the following concentrations:

| x—x | without (+) STB |
|---|---|
| ●—● | (+) STB 6, 5 · 10$^{-6}$ M |
| ○—○ | (+) STB 6, 1 · 10$^{-5}$ M |
| ■—■ | (+) STB 6, 5 · 10$^{-5}$ M |
| ▲—▲ | (+) STB 6, 1 · 10$^{-4}$ M |

The data given in this figure are the averages ±sm of four experiments.

In addition the racemic STB compounds behave as powerful non-competitive antagonists of phenylephrine. About this reference can be made to page 40 of No. FR-A-2,469,413.

(3) Study of the inhibition of the sympathetic excitation in vivo

This study was made for the most hypotensive derivative, STB 6. The vascular reactivity of the mesenteric territory perfused in situ in the rat was measured (according to Jackson and Campbell, Eur. J. Pharmacol., 1980, 66, 217-224). After anesthetizing of the rat with pentothal (40 mg.kg$^{-1}$ i.p.) the mesenteric territory was perfused at constant flow from a catheter diverting the blood stream of the abdominal aorta. The vasoconstrictor activity resulting from periarterial electrical excitation of the sympathetic nerves (7 Hz) and from of noradrenalin (200 ng) into the catheter introduction was measured. The activities of the Berbine derivatives administered intravenously were determined for the two types of pressure response. The results obtained are shown in FIGS. 4a and 4b in which the average blood pressure $\Delta P$ mm Hg is plotted on the ordinates and time plotted on the abscissae, the injection of the product to be tested or of the placebo (constituted by the same volume of physiological serum) being at time 0.

Figure 4A:
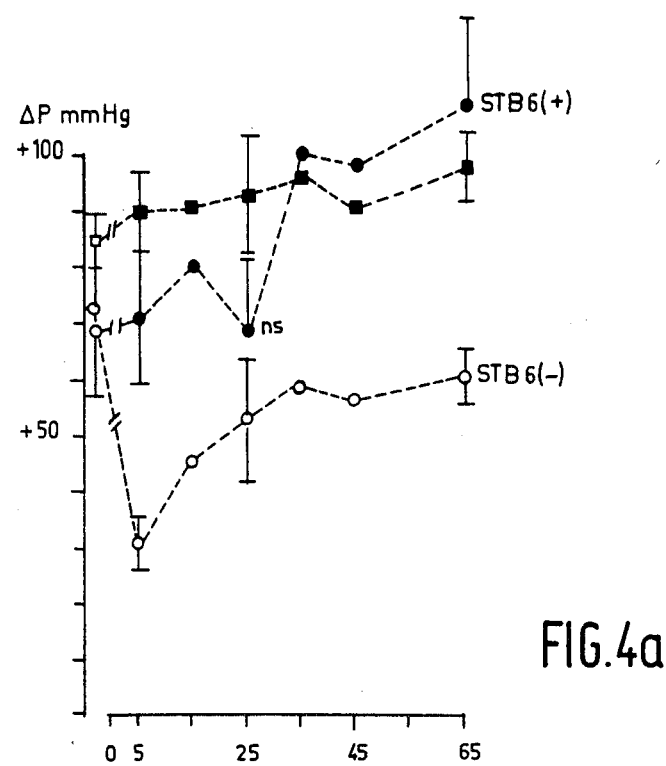
FIGS. 4a and 4b illustrate the vasoconstriction caused by electrical stimulation and noradrenalin, respectively.
Figure 4B:
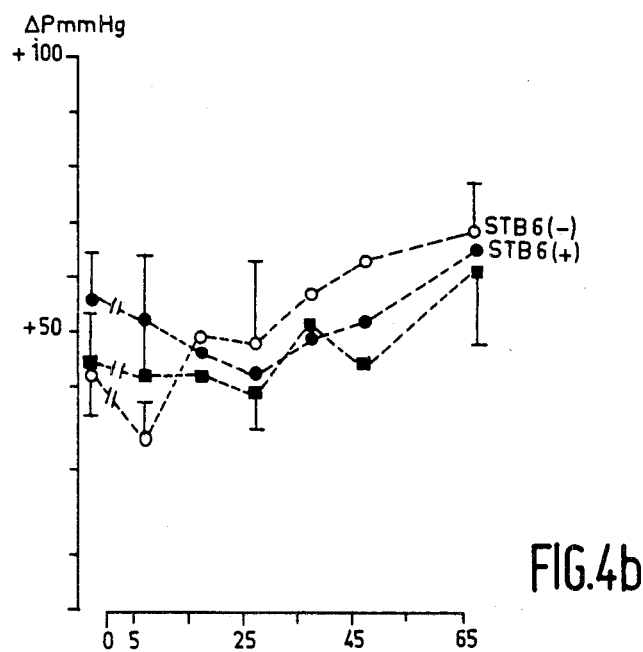

FIG. 4a relates to the vasoconstriction caused by electrical stimulation and FIG. 4b to that caused by noradrenalin.

The ●—● curves relate to (+) STB 6.
The ○—○ curves relate to (−) STB 6.
The ■—■ curves relate to the placebo.

The results are the average ±sm of 5 assays. It can be deduced from FIG. 4 that the (−) STB 6 derivative, administered at an i.v. dose of 0.5 mg.kg$^{-1}$, decreases the vasoconstriction of the mesenteric territory caused by the electrical stimulation of the sympathetic nerves, without modifying the pressure response due to noradrenalin injection. The (+) STB 6 derivative administered under the same conditions and at the same dose does not have a significant activity. These results show that (−) STB 6 inhibits in vivo either the release of endogenous mediators induced by nerve excitation, or the pressure response to these mediators, without affecting the vasoconstriction induced by exogenous noradrenalin. (+) STB 6 does not have this activity under the same experimental conditions.

The above tests show that the (−) Berbine derivatives exhibited hypotensive activity and competitively inhibit the vasoconstrictor activity of phenylephrine ($\alpha$-blocking activity). Both these activities are sterospecific. The (−) isomer of STB 6, the most hypotensive of the derivatives studied, reduces the pressure response to sympathetic excitation whereas the (+) isomer is devoid of this activity at the same doses. The (+) isomer behaves like a non-competitive antagonist of phenylephrine on the isolated rat aorta.

(4) Study of the binding selectivity of the enantiomers of Berbine and its derivatives to the $\alpha_1$ and $\alpha_2$ adrenergic receptors The tests were carried out on rat cerebral cortex homogenate, according to the method described by P. Greengross and R. Bremmerclaus, Eur. J. Pharmacol. (1979) 55 323-326.

The ligands used were, respectively, $^3$H-prazosin for the $\alpha_1$ receptors ($K_D$ 0.138±0.02 nmole. 1$^{-1}$, maximum binding 200±21 fmoles.mg protein$^{-1}$) and $^3$H-yohimbin for the $\alpha_2$ receptors ($K_D$=10.2 nmole.1$^{-1}$, maximum binding 172.5±49.9 fmoles.mg protein$^{-1}$). The results represent the average of the three assays. The Ki values were calculated according to Cheng and Prussoff (Biochem. Parmacol. 1973 22 3099-3108).

| | SPECIFIC BINDING, Ki, nmole · 1$^{-1}$ | |
|---|---|---|
| | $\alpha$ 1 | $\alpha$ 2 |
| Prazosin | 0.15 ± 0.03 | 382 ± 66 |
| Yohimbin | 322 ± 26 | 13.7 ± 3.6 |
| Berbine (−) | 212 ± 26 | 140 ± 44 |
| (−) STB 6 | 419 ± 132 | 1015 ± 335 |
| (−) STB 4 | 462 ± 10 | 307 ± 118 |
| Berbine (+) | 4730 ± 538 | 569 ± 137 |
| (+) STB 6 | 2931 ± 363 | 901 ± 299 |
| (+) STB 4 | 1220 ± 175 | 321 ± 72 |

It can be seen that the dextrorotatory and levorotatory isomers of Berbine have comparable affinities for the $\alpha_1$ and $\alpha_2$ receptors, whereas the levorotatory isomer of 10,11-dimethoxy-3-hydroxy-5,6,13,13a-tetrahydro-8H-dibenzo-[a,g]-quinolizine has a strong affinity for the $\alpha_1$ receptor, with respect to that for the $\alpha_2$ receptor.

Toxicity:

The LD$_{50}$ was determined in the mouse. The derivatives to be tested were administered in aqueous solution containing 7% dimethylformamide, by esophageal forced feeding of 0.4 ml per 20 g of body weight, to male mice weighing 20 to 25 g. Under these conditions the LD$_{50}$ of (−) STB 6 is in the range from 200 and 300 mg.kg$^{-1}$ while that of (−) STB 52 is greater than 800 mg.kg$^{-1}$ (30% mortality at this dose, limit of solubility). The corresponding (+) derivatives do not cause any deaths at a dose of 800 mg.kg$^{-1}$ (limit of solubility).

The compounds according to the invention have therefore pharmacological properties which allow their use in the cardiovascular area. The doses to be administered vary according to the condition of the patient and the cardiovascular disorder to be treated. Nevertheless, doses of 0.2 to 0.3 g per day are convenient.

What is claimed is:

1. Levorotatory enantiomers of derivatives of 5,6,13,13a-tetrahydro-8H-dibenzo-[a,g]-quinolizine and their pharmaceutically acceptable salts which are competitive inhibitors of alpha-adrenergic receptors, having the formula III:

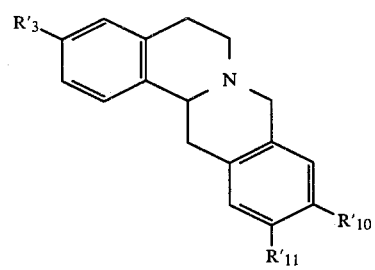

in which:
R'$_3$ is hydrogen, a cyclic or alkyl group or an —OR or —SR moiety wherein R is hydrogen, a cyclic or alkyl group or a group of formula:

wherein R" is a phenylalkyl, alkyl or cyclic group, R'$_{10}$ and R'$_{11}$, which are identical or different, represent hydrogen, a cyclic-oxy, or alkoxy or hydroxy group, or R'$_{10}$ and R'$_{11}$ taken together form a group —O—(CH$_2$)$_n$—O— in which n is 1 to 3, provided that R'$_3$, R'$_{10}$ and R'$_{11}$ are not simultaneously hydrogen, further provided that when R'$_{10}$ and R'$_{11}$ are hydrogen, R'$_3$ is not an alkoxy group, and provided that when R'$_3$ is hydrogen, R'$_{10}$ and R'$_{11}$ are not methoxy or hydroxy, wherein alkyl designates a straight or branched aliphatic hydrocarbon group having 1 to 12 carbon atoms, and a cyclic group refers to a phenyl, benzyl, furan, pyridine, oxazole, cyclohexane, tetrahydrofuran, piperidine, or oxazolidine group.

2. A levorotatory enantiomer according to claim 1 which is 3-hydroxy-5,6,13,13a-tetrahydro-8H-dibenzo-[a,g]-quinolizine or its pharmaceutically acceptable salts.

3. A levorotatory enantiomer according to claim 1 which is 10,11-dimethoxy-3-hydroxy-5,6,13,13a-tetrahydro-8H-dibenzo-[a,g]quinolizine, or its pharmaceutically acceptable salts.

4. Esters of the compounds according to claim 3 wherein R'$_3$ of formula III represents a benzyl group.

5. A pharmaceutical composition comprising as the active ingredient, a levorotatory enantiomer of a derivative of 5,6,13,13a-tetrahydro-8H-dibenzo-[a,g]-quinolizine and its pharmaceutically acceptable salts which are competitive inhibitors of alpha-adrenergic receptors, having the formula III:

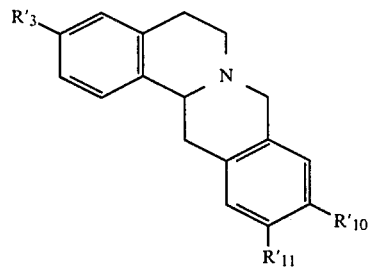

in which:
R'$_3$ is hydrogen, a cyclic or alkyl group or an —OR or —SR moiety wherein R is hydrogen, a cyclic or alkyl group or a group of formula: R"—C—, wherein R" is a phenylalkyl, alkyl or cyclic group,
R'$_{10}$ and R'$_{11}$, which are identical or different, represent hydrogen, a cyclic-oxy, or alkoxy or hydroxy group, or R'$_{10}$ and R'$_{11}$ taken together form a group —O—(CH$_2$)$_n$—O— in which n is 1 to 3, provided that R'$_3$, R'$_{10}$ and R'$_{11}$ are not simultaneously hydrogen, further provided that when R'$_{10}$ and R'$_1$ are hydrogen, R'$_3$ is not an alkoxy group, and provided that when R'$_3$ is hydrogen, R'$_{10}$ and R'$_{11}$ are not methoxy or hydroxy, wherein alkyl designates a straight or branched aliphatic hydrocarbon group having 1 to 12 carbon atoms, and a cyclic group refers to a phenyl, benzyl, furan, pyridine, oxazole, cyclohexane, tetrahydrofuran, piperidine, or oxazolidine group.

6. A pharmaceutical composition according to claim 5, in unit dosage form for the treatment of cardiovascular disorders and arterial hypertension.

* * * * *